(12) United States Patent
England et al.

(10) Patent No.: US 9,034,628 B2
(45) Date of Patent: *May 19, 2015

(54) INDUCTION OF GENE EXPRESSION USING A HIGH CONCENTRATION SUGAR MIXTURE

(75) Inventors: George R. England, Redwood City, CA (US); Aaron Kelley, Mountain View, CA (US); Colin Mitchinson, Half Moon Bay, CA (US)

(73) Assignee: Danisco US Inc., Palo Alto, CA (US)

( * ) Notice: Subject to any disclaimer, the term of this patent is extended or adjusted under 35 U.S.C. 154(b) by 298 days.

This patent is subject to a terminal disclaimer.

(21) Appl. No.: 13/029,940

(22) Filed: Feb. 17, 2011

(65) Prior Publication Data
US 2011/0207913 A1   Aug. 25, 2011

Related U.S. Application Data

(63) Continuation of application No. 12/498,102, filed on Jul. 6, 2009, now abandoned, which is a continuation of application No. 10/660,123, filed on Sep. 10, 2003, now Pat. No. 7,713,725.

(60) Provisional application No. 60/409,466, filed on Sep. 10, 2002.

(51) Int. Cl.
| | |
|---|---|
| *C12N 1/20* | (2006.01) |
| *C07K 14/00* | (2006.01) |
| *C12P 21/06* | (2006.01) |
| *C12P 19/12* | (2006.01) |
| *C12N 1/14* | (2006.01) |
| *C12N 1/38* | (2006.01) |
| *C12P 19/14* | (2006.01) |
| *C12P 21/02* | (2006.01) |
| *C12N 9/42* | (2006.01) |

(52) U.S. Cl.
CPC . *C12P 19/12* (2013.01); *C12N 1/14* (2013.01); *C12N 1/38* (2013.01); *C12P 19/14* (2013.01); *C12P 21/02* (2013.01); *C12Y 302/01021* (2013.01); *C12N 9/2437* (2013.01); *C12N 9/2445* (2013.01)

(58) Field of Classification Search
None
See application file for complete search history.

(56) References Cited

U.S. PATENT DOCUMENTS

| | | | |
|---|---|---|---|
| 3,972,775 A * | 8/1976 | Wilke et al. | 435/99 |
| 4,486,553 A | 12/1984 | Wesch | |
| 4,908,311 A * | 3/1990 | Sasaki et al. | 435/101 |
| 5,472,864 A | 12/1995 | Bower | |
| 5,541,097 A | 7/1996 | Lantero et al. | |
| 5,610,034 A | 3/1997 | Nyyssonen et al. | |
| 6,255,115 B1 | 7/2001 | Beijersbergen et al. | |
| 6,268,328 B1 | 7/2001 | Mitchinson et al. | |
| 6,352,841 B1 | 3/2002 | Lehmbeck | |
| 6,407,046 B1 | 6/2002 | Fowler et al. | |
| 6,558,693 B1 | 5/2003 | Knap et al. | |
| 6,566,112 B2 | 5/2003 | Jones et al. | |
| 6,579,841 B1 | 6/2003 | Day et al. | |
| 6,582,750 B2 | 6/2003 | Fowler et al. | |
| 7,713,725 B2 | 5/2010 | England et al. | |
| 2010/0009408 A1 | 1/2010 | England et al. | |

FOREIGN PATENT DOCUMENTS

| | | |
|---|---|---|
| EP | 0137280 | 4/1985 |
| EP | 0215594 | 3/1997 |
| JP | 05211883 | 8/1993 |
| WO | WO 92/01047 | 1/1992 |
| WO | WO 96/23928 | 8/1996 |
| WO | WO 02/064624 | 8/2002 |

OTHER PUBLICATIONS

Alexopoulous, C.J., (1962), Introductory Mycology, New York: Wiley.
Ausubel et al., Current Protocols in Molecular Biology, Greene Publishing, Associates and Wiley Interscience, N.Y. (1994).
Hopwood et al., "Genetic Manipulation of *Streptomyces*: A Laboratory manual," Innes, 1985.
Kriegler, Gene Transfer and Expression: A Laboratory Manual, 1990.
Sambrook, et al., Molecular Cloning: A Laboratory Manual (Second Edition), Cold Spring Harbor Press, Plainview, N.Y., 1989.
Allen and Mortensen, Biotechnol. Bioeng. (1981) 2641-2645.
Bajar, Aslam et al., "Identification of a fungal cutinase promoter that is inducible by a plant signal via a phosphorylated trans-acting factor," Proc. Natl. Acad. Sci. USA, (1991) 88: 8208-8212.
Ballance, D.J. et al., "Transformation of *Aspergillus nidulans* by the Orotidine-5'-Phosphate Decarboxylase Gene of *Neurospora crassa*," Biochemical and Biophysical Research Communications, (1983) 112(1): 284-289.
Barclay, Stephen L. et al., "Efficient Transformation of *Dictyostelium discoideum* Amoebae," Molecular and Cellular Biology, (1983) 3: 2117-2130.
Boel, E. et al., "Two different types of intervening sequences in the glucoamylase gene from *Aspergillus niger*," The EMBO Journal (1984) 3(7): 1581-1585.

(Continued)

*Primary Examiner* — Robert A Zeman
(74) *Attorney, Agent, or Firm* — Danisco US Inc.

(57) ABSTRACT

Described herein is a composition useful for inducing expression of genes whose expression is under control of an inducible promoter sequence and methods for the compositions preparation and use.

11 Claims, 2 Drawing Sheets

(56) References Cited

OTHER PUBLICATIONS

Brigidi, P. et al., "Genetic Transformation of intact cells of *Bacillus subtilis* by electroporation," FEMS Microbiology Letters, (1990) 67: 135-138.
Bull, John H. et al., "Heavily methylated amplified DNA in transformants of *Neurospora crassa*," Nature, (1984) 310:701-704.
Case, Mary E. et al., "Efficient transformation of *Neurospora crassa* by utilizing hybrid plasmid DNA," Proc. Natl. Acad. Sci. USA, (1979) 76(10): 5259-5263.
Evan, Gerard I. et al., "Isolation of Monoclonal Antibodies Specific for Human c-*myc* Proto-Oncogene Products," Molecular and Cellular Biology, (1985) 5(12): 3610-3616.
Field, Jeffrey et al., "Purification of a *RAS*-Responsive Adenylyl Cyclase Complex from *Saccharomyces cerevisiae* by Use of an Epitope Addition Method," Molecular and Cellular Biology, (1988) 8(5): 2159-2165.
Goldman, G.H. et al., "Transformation of *Trichoderma harzianum* by high-voltage electric pulse," Current Genetics, (1990) 17: 169-174.
Hopp, Thomas P. et al., "A Short Polypeptide Marker Sequence Useful for Recombinant Protein Identification and Purification," Biotechnology, (1988) 6: 1204-1210.
Hynes, Michael J. et al., "Isolation of Genomic Clones Containing the *amd*S Gene of *Aspergillus nidulans* and Their Use in the Analysis of Structural and Regulatory Mutations," Molecular and Cellular Biology, (1983) 3:1430-1439.
Ilmen, Marja et al. "Regulation of Cellulase Gene Expression in the Filamentous Fungus *Trichoderma reesei*," Applied and Environmental Microbiology, (1997) 63(4): 1298-1306.
Innis, M.A. et al., "Expression, Glycosylation, and Secretion of an *Aspergillus* Glucoamylase by *Saccharomyces cerevisiae*," Science (1985) 228: 21-26.
International Search Report for PCT/US03/28438 filed Sep. 10, 2003.
John, Marion A., et a., "Transformation of *Aspergillus nidulans* using the *arg*B gene," Enzyme Microb. Technol., (1984) 6: 386-389.
Johnstone, I.L. et al., "Cloning an *Aspergillus nidulans* developmental gene by transformation," The EMBO Journal (1985) 4(5): 1307-1311.
Ju, Lu-Kwang et al., "Wastepaper Hydrolysate as Soluble Inducing Substrate for Cellulase Production in Continuous Culture of *Trichoderma reesei*," Biotechnol. Prog. (1999) 15: 91-97.
Kelly, Joan M. et al., "Transformation of *Aspergillus niger* by the *amd*S gene of *Aspergillus nidulans*," The EMBO Journal (1985) 4(2): 475-479.
Kinsey, John A. et al., "Transformation of *Neurospora crassa* with the Cloned *am* (Glutamate Dehydrogenase) Gene," Molecular and Cellular Biology (1984) 4(1): 117-122.
Lockington, Robin A. et al., "Cloning and characterization of the ethanol utilization regulon in *Aspergillus nidulans*," Gene (1985) 33: 137-149.
Lorito, M. et al, "Biolistic transformation of *Trichoderma harzianum* and *Gliocladium virens* using plasmid and genomic DNA," Current Genetics (1993) 24: 349-356.
Lutz-Freyermuth, Carol et al, "Quantitative determination that one of two potential RNA-binding domains of the A protein component of the U1 small nuclear ribonucleoprotein complex binds with high affinity to stem-loop II of U1 RNA," Proc. Natl. Acad. Sci. USA (1990) 87: 6393-6397.
Mandels, Mary, "Applications of Cellulases," Biochemical Society Transactions, (1985) 13(2): 414-416.

Marlin, George A. et al., "GAP Domains Responsible for Ras p21-Dependent Inhibition of Muscarinic Atrial K+ Channel Currents," Science (1992) 255: 192-194.
McKnight, Gary L. et al., "Nucleotide Sequence of the Triosephosphate Isomerase Gene from *Aspergillus nidulans*: Implications for a Differential Loss of Introns," Cell (1986) 46: 143-147.
Mullaney, Edward J. et al., "Primary structure of the *trp*C gene from *Aspergillus nidulans*," Mol. Gen. Genet., (1985) 199: 37-45.
Nevalainen, H. et al., "Molecular Biology of Cellulolytic Fungi," The Mycota II, Genetics and Biotechnology, Kück (Ed.), Springer-Verlag Berlin Heidelberg, 1998, pp. 303-319.
Nunberg, Jack H. et al., "Molecular Cloning and Characterization of the Glucoamylase Gene of *Aspergillus awamori*," Molecular and Cellular Biology (1984) 4: 2306-2315.
Nyyssonen, Eini et al., "Efficient Production of Antibody Fragments by the Filamentous Fungus *Trichoderma reesei*," Bio/Technology (1993) 11: 591-595.
Paborsky, Lisa R., "Mammalian cell transient expression of tissue factor for the production of Antigen," Protein Engineering (1990) 3(6): 547-553.
Pentilla, Merja E. et al., "A versatile transformation system for the cellulolytic filamentous fungus *Trichoderma reesei*," Gene (1987) 61: 155-164.
Scopes, Robert K. et al., "Purification of All Glycolytic Enzymes from One Muscle Extract," Methods Enzymol. (1982) 90: 479-491.
Seiboth, B. et al. "Lactose metabolism and cellulose production in *Hypocrea jecorina*: the gal7 gene, encoding galactose-1-phosphate uridylyltransferase, is essential for growth on galactose but not for cellulose induction," Mol. Genet. Genomics, (2002) 267: 124-132.
Sheir-Neiss, G. et al., "Characterization of the secreted Cellulases of *Trichoderma reesei* wild type and mutants during controlled fermentation," Appl. Microbiol. Biotechnol. (1984) 20: 46-53.
Skinner, Richard H. et al., "Use of the Glu-Glu-Phe C-terminal Epitope for Rapid Purification of the Catalytic Domain of Normal and Mutant *ras* GTPase-activating Proteins," The Journal of Biological Chemistry (1991) 266(22): 14163-14166.
Tilburn, Joan et al., "Transformation by integration in *Aspergillus nidulans*," Gene (1983) 26: 205-221.
Yelton, M. Melanie et al., "Transformation of *Aspergillus nidulans* by using a *trp*C plasmid," Proc. Natl. Acad. Sci. USA (1984) 81: 1470-1474.
Allen Biotech & Bioeng. Symp. (1980) 10: 189-197.
Dechamps & Huet, Biotech Letters (1984) 6: 55-60.
Sternberg D., Applied & Environmental Micro. (1976) 31(5): 648-654.
Sternberg D., Can J. Microbial. (1977) 23: 139-147.
Suto M., Journal of Bioscience and Bioeng. (2001) 92(4): 305-311.
Vaheri, M., Biotechnology Letter (1979) 1(1): 41-46.
EP Office Action re 03796327.9 dated Jan. 23, 2009.
EP Office Action re 03796327.9 dated Aug. 24, 2009.
Claeyssens, M. et al., "Studies of the cellulolytic system of the filamentous fungus *Tricoderma reesei* QM 9414" Biochem. J. (1990) 270, 251-256.
Sternberg, David, et al. "Regulation of the Cellulolytic System in *Tricoderma reesei* by Sophorose: Induction of Cellulase and Repression of β-Glucosidase" Journal of Bacteriology, Dec. 1980, p. 1197-1199 vol. 144, No. 3.

* cited by examiner

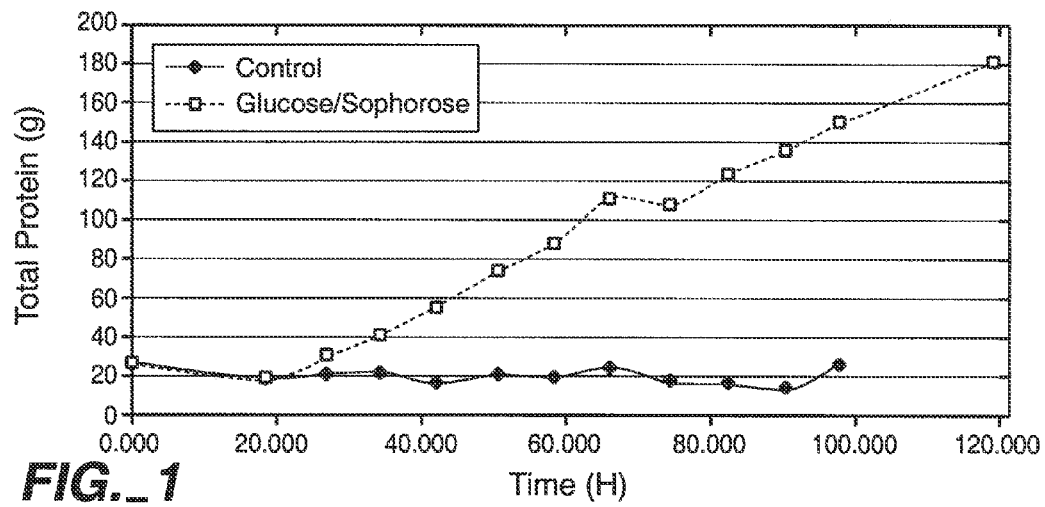
FIG._1
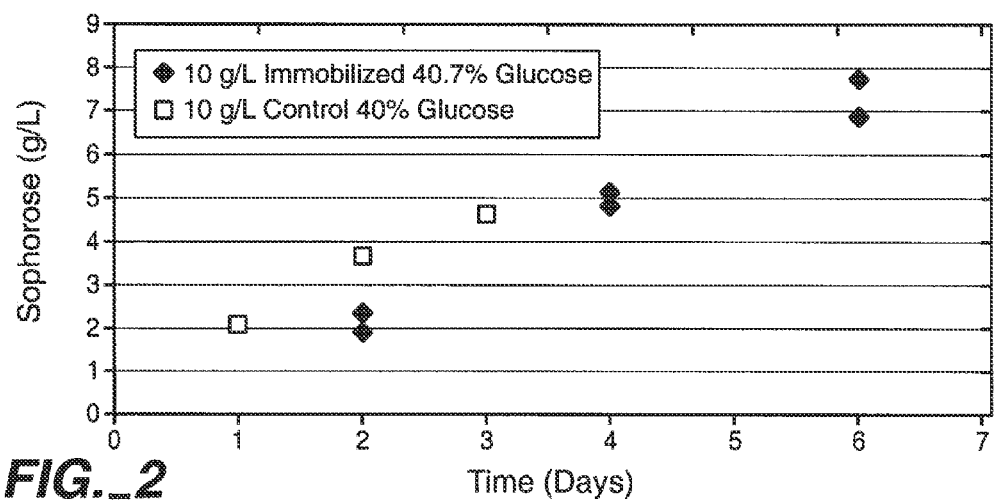
FIG._2
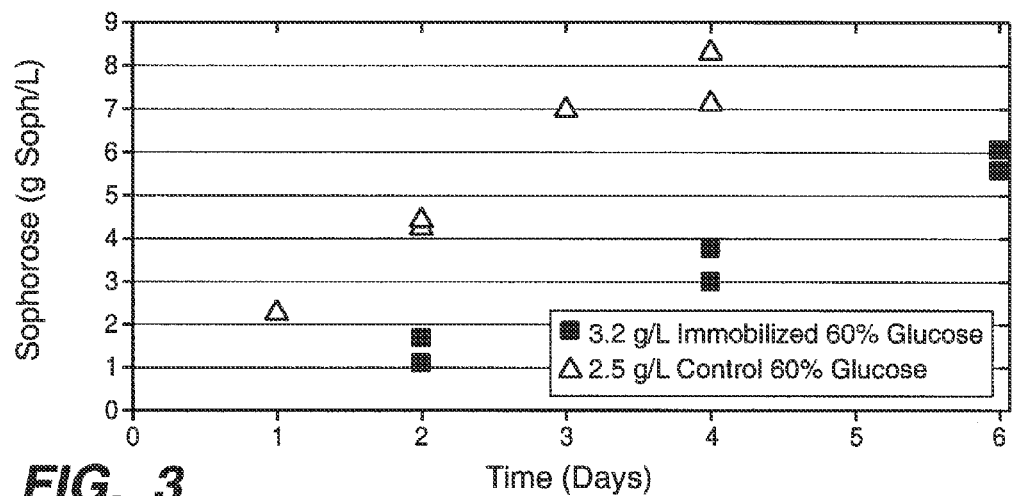
FIG._3

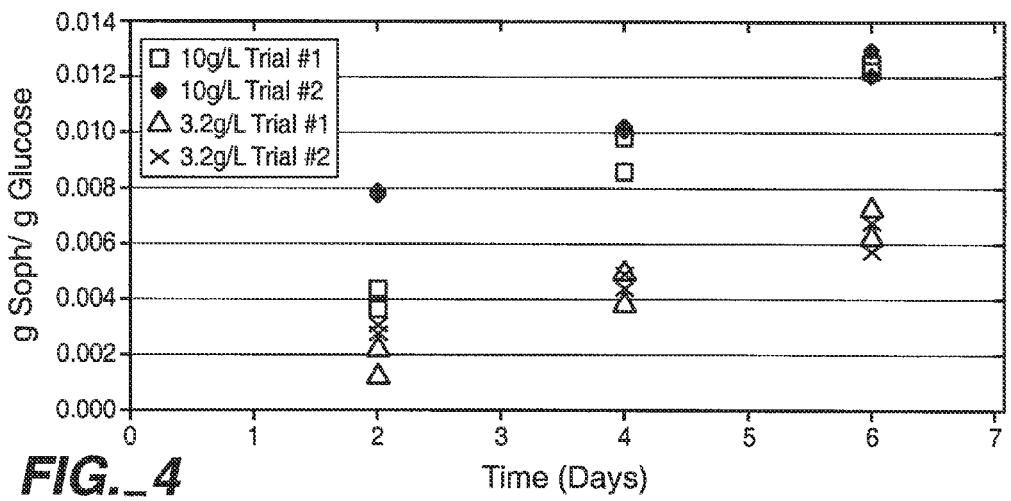
FIG._4
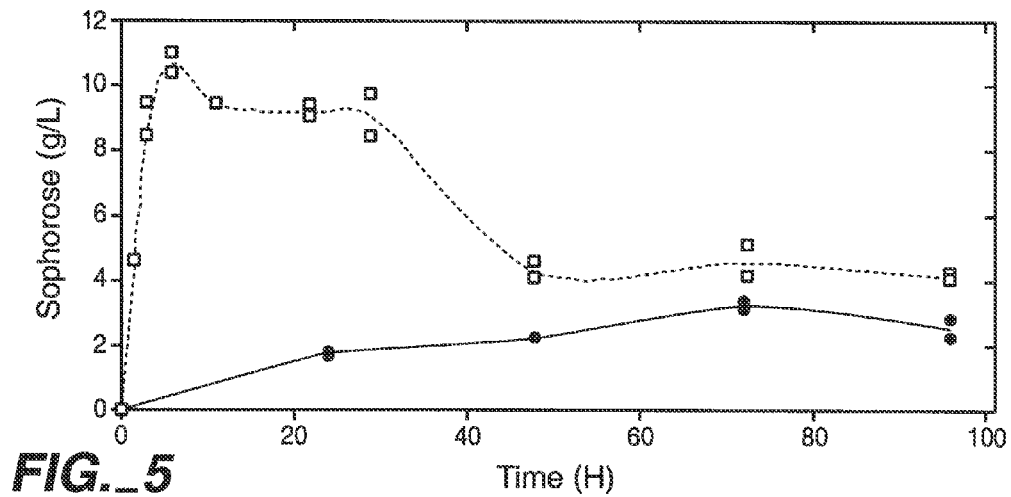
FIG._5
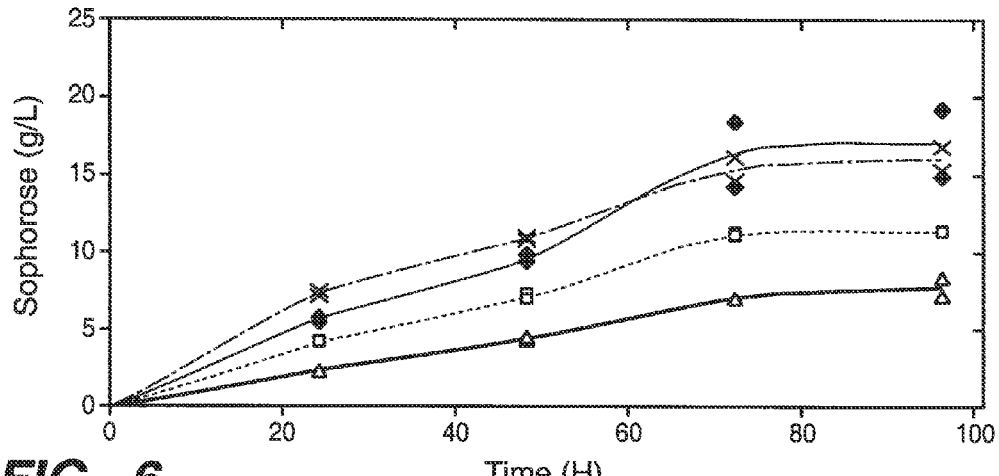
FIG._6

INDUCTION OF GENE EXPRESSION USING A HIGH CONCENTRATION SUGAR MIXTURE

CROSS-REFERENCE TO RELATED APPLICATIONS

This application is a continuation of U.S. patent application Ser. No. 12/498,102, filed Jul. 6, 2009, which is a continuation of U.S. patent application Ser. No. 10/660,123, filed Sep. 10, 2003, now U.S. Pat. No. 7,713,725, which claims the benefit of U.S. Provisional Application No. 60/409,466, filed Sep. 10, 2002, which are herein incorporated in their entirety by reference.

STATEMENT AS TO RIGHTS TO INVENTIONS MADE UNDER FEDERALLY SPONSORED RESEARCH AND DEVELOPMENT

Portions of this work were funded by Subcontract No. ZCO-0-30017-01 with the National Renewable Energy Laboratory under Prime Contract No. DE-AC36-99GO10337 with the U.S. Department of Energy. Accordingly, the United States Government may have certain rights in this invention.

FIELD OF THE INVENTION

This invention relates to methods for improved production of proteins from a cell culture. The inventors have discovered culture components and conditions that dramatically increase the amount of protein produced from genes under the control of cellulase gene promoter sequences. The improved methods can be used for the production of proteins encoded by naturally occurring cellulase genes as well as from various heterologous constructs.

BACKGROUND OF THE INVENTION

Filamentous fungi and cellulolytic bacteria produce extracellular cellulase enzymes that confer on the organisms the ability to hydrolyze the β-(1,4)-linked glycosidic bonds of cellulose to produce glucose. These enzymes provide the organisms with the ability to use cellulose, the most abundant plant polysaccharide, for growth.

The filamentous fungus, *Trichoderma reesei*, is an efficient producer of cellulase enzymes. As such *Trichoderma reesei* has been exploited for its ability to produce these enzymes, which are valuable in the production of such commodities as fuel ethanol, clothing, detergents, fibers and other products.

The cellulolytic mix of *Trichoderma reesei* proteins is among the best characterized cellulolytic pathways of microorganisms. The cellulases that comprise these mixes are classified into two broad categories: the endoglucanases (EG) and the cellobiohydrolases (CBH). β-glucosidase is also part of the cellulase mix of *Trichoderma reesei*.

*Trichoderma reesei* has also been exploited for its ability to produce heterologous proteins. Genes encoding a desired protein can be regulated when they are operably linked to the inducible cbh1 promoter of *T. reesei*. Foreign polypeptides have been secreted in *Trichoderma reesei* as fusions with the catalytic domain plus linker region of cbh1 (Nyyssonen et al., Bio/technology 11:591-595, 1993).

Expression of the genes comprising the cellulase system is coordinate and regulated at the transcriptional level. The members of this system act synergistically, and as noted above, are necessary for the efficient hydrolysis of cellulose to soluble oligosaccharides.

Expression and production of the main cellulase genes in *Trichoderma*, cbh1, cbh2, egl1, and egl2, is dependent on the carbon source available for growth. The cellulase genes are tightly repressed by glucose and are induced several thousand fold by cellulose or the disaccharide sophorose. Indeed, the expression level of the major cellobiohydrolase 1 (cbh1) is up-regulated several thousand fold on media containing inducing carbon sources such as cellulose or sophorose compared with glucose containing media (Ilmen et al., App. Environ. Microbio., 1298-1306, 1997).

Commercial scale production of cellulase enzymes is by either solid or submerged culture including batch, fed batch, and continuous flow processes. The most problematic and expensive aspect of industrial cellulase production is providing the appropriate inducer to *Trichoderma*. As is the case for laboratory scale experiments, cellulase production on a commercial scale is induced by growing the fungus on solid cellulose or by culturing the organism in the presence of a disaccharide inducer such as lactose. Unfortunately on an industrial scale, both methods of induction have drawbacks which result in high costs being associated with cellulase production.

Cellulase synthesis is subject to both cellulose induction and glucose repression. Thus, a critical factor influencing the yield of cellulase enzymes or heterologous proteins under the control of an inducible promoter is the maintenance of a proper balance between cellulose substrate and glucose concentration; it is critical for obtaining reasonable commercial yields of the regulated gene product. Although cellulose is an effective and inexpensive inducer, controlling the glucose concentration when *Trichoderma* is grown on solid cellulose can be problematic. At low concentrations of cellulose, glucose production may be too slow to meet the metabolic needs of active cell growth and function. On the other hand, cellulase synthesis can be halted by glucose repression when glucose generation is faster than consumption. Thus, expensive process control schemes are required to provide slow substrate addition and monitoring of glucose concentration (Ju and Afolabi, Biotechnol. Prog., 91-97, 1999). Moreover, the slow continuous delivery of substrate can be difficult to achieve as a result of the solid nature of the cellulosic materials.

Allen and Mortensen (Biotechnol. Bioeng., 2641-45, 1981) have shown that 200 IU/ml of purified β-glucosidase from *Aspergillus phoenicis* when incubated with a 50% glucose syrup produces a solution with the ability to induce cellulase production when used as a carbon source. Purification of the β-glucosidase is both time-consuming and expensive. In addition, these authors used more than 20× the β-glucosidase loading compared to that used in this current work.

Some of the problems associated with the use of cellulose as an inducing substrate can be overcome through the use of soluble substrates and inducers such as lactose or sophorose. Lactose has to be provided at high concentrations so as to function as an inducer and a carbon source. (See Seiboth, et. al., Mol. Genet. Genomics, 124-32, 2002.) Gentiobiose may also serve as an inducer. Sophorose is a more potent inducer than cellulose, but sophorose is expensive and difficult to manufacture. Thus, while it is easier to handle and control than solid cellulose, sophorose can nonetheless make the cost of producing cellulases prohibitively expensive and, thus, is impractical for commercial cellulase production. Clearly, a need exists for a convenient, soluble substrate composition that also provides an inexpensive method of cellulase induction in filamentous fungi, e.g., *Trichoderma reesei*.

In addition, the ability to regulate inducible promoters to express either endogenous or heterologous genes with an inexpensive inducing agent would of great commercial benefit.

BRIEF SUMMARY OF THE INVENTION

It has now been discovered that when a whole cellulase preparation is added to a concentrated glucose solution, and the composition is incubated for at least two days at 50° C. to about 65° C., a sugar mixture containing appreciable quantities of an inducer of cellulase gene expression is produced. Surprisingly, the resulting complex mixture is sufficient to induce cellulase production as is without further purification. This discovery is surprising since glucose acts as a repressor of cellulase genes in *Trichoderma reesei*. This discovery provides an inducer of cellulase gene expression that is an inexpensive alternative to lactose or purified sophorose and a less cumbersome alternative to solid cellulose for the production of cellulases in *Trichoderma reesei*.

In one embodiment the invention provides a composition for inducing expression of genes whose expression is under control of cellulase gene promoter sequences, comprising: (i) from about 5% to about 75% (wt/wt) glucose, preferably 50%-70% glucose and (ii) from about 2 g/L to about 10 g/L total protein, preferably 5 g/L of whole cellulase preparation wherein the composition is incubated at about 50° C. to about 70° C. for several days prior to use to promote formation within the composition of an inducer of gene expression.

In another embodiment the inducing feed composition is incubated at about 50° C. to about 65° C., preferably at about 55° C. for 48 hours before use.

In another embodiment the inducing feed composition is incubated at about 50° C. to about 65° C., preferably at about 65° C. for 72 hours before use.

In a preferred embodiment the incubation product that results from incubating a concentrated glucose solution with whole cellulase preparation, is a mixture of sugars containing sophorose. In another preferred embodiment the incubation product is a mixture of sugars containing gentiobiose.

In one embodiment the invention provides a method for producing proteins whose gene expression is under control of an inducible promoter sequence, wherein a cell culture is provided, and an inducing feed composition resulting from incubation of a whole cellulase preparation in a concentrated glucose solution is added to the culture in an amount effective for inducing the expression of genes under control of the inducible promoter sequence.

The improved methods can be used for the production of proteins encoded by naturally occurring cellulase genes as well as from various heterologous constructs. Such constructs include expression vectors wherein the gene encoding the protein of interest is operably linked to an inducible promoter. In one embodiment, the inducible promoter is a cellulase gene promoter. In a second embodiment, the inducible promoter is a sophorose-inducible promoter. In a third embodiment, the inducible promoter is a gentiobiose-inducible promoter. In one aspect, the inducible promoter is a cbh 1 promoter.

In an embodiment the method for producing a protein of interest produces a protein selected from the group consisting of hormones, enzymes, growth factors, cytokines, and antibodies. In one aspect, the method is used to produce proteins that are naturally occurring cellulase enzymes. In another aspect, the method is used to produce proteins whose expression is not naturally under control of cellulase gene promoter sequences.

In another embodiment, the method for producing proteins employs a filamentous fungus. In one aspect the fungus is *Trichoderma*. In another aspect, the fungus is *Trichoderma reesei*.

In a further embodiment the method for producing a protein of interest utilizes an inducing composition produced by adding a whole cellulase preparation to a cellobiose solution, and the cellulase-cellobiose solution is incubated for at least two days at 50° C. to about 70° C. to form an inducing feed composition. In one aspect the solution is incubated for at least two days at 50° C. to about 65° C. to form an inducing feed composition. This composition is a sugar mixture containing appreciable quantities of an inducer of cellulase gene expression.

BRIEF DESCRIPTION OF THE DRAWINGS

FIG. 1 illustrates the effects on wild-type *T. reesei* (RLP-37) (see Sheir-Neiss and Montenecourt, Appl. Microbio. Biotechnol., 46-53, 1984) cellulase production of feeding the inventive inducing composition (■; squares) compared with a glucose composition (♦; diamonds).

FIG. 2 is a graph that illustrates the differences between the production of sophorose by immobilized enzyme (■; squares) compared with an enzyme solution (♦; diamonds). The final glucose concentration is approximately 40%. The protein loading was 10 g/L. See example 4 for details.

FIG. 3 is a graph that illustrates the differences between the production of sophorose by immobilized enzyme (■; squares) compared with an enzyme solution (▲; triangles). The final glucose concentration is approximately 60%. The protein loading was 3.2 g/L. See example 4 for details.

FIG. 4 is a graph comparing the results from a second run of the experiments with the first run of experiments described for FIGS. 2 and 3 that used the same immobilized enzyme. The immobilized enzyme recovered after the first run retained activity in the second run. Symbols are: ■ (squares), first run of 10 g/L experiment; ♦ (diamonds), second run of 10 g/L experiment; ▲ (triangles), first run of 3.2 g/L experiment; X, second run of 3.2 g/L experiment.

FIG. 5 is a graph showing sophorose production in 25% Cellobiose compared to 25% glucose. Sophorose production in 25% cellobiose (■; squares) or glucose solution (w/w) (●; circles).

FIG. 6 is a graph showing sophorose production in 60% glucose solution (w/w) at different loadings of whole cellulase. ▲ (triangles), 2.5 g/L, ■ (squares), 5.0 g/L, ♦ (diamonds), 7.5 g/L, X, 10 g/L whole cellulase.

DETAILED DESCRIPTION

The filamentous fungus *Trichoderma reesei* is one of the most extensively studied cellulolytic organisms (reviewed e.g. by Nevalainen and Penttila, Mycota, 303-319, 1995). In industry, the cellulolytic enzymes of *Trichoderma* are used for many purposes including; production of fuel ethanol, paper, rayon, cellophane, detergents and fibers. Cellulase enzymes are also used to improve the nutritional value of animal feeds, and to facilitate the extraction of valuable components from plant cells (Mandels, Biochem. Soc. Trans., 414-16. 1985). Thus, these enzymes are of primary importance in the production of many useful products.

The production of cellulases in *Trichoderma* is dependent on the carbon source available. Cellulose, lactose and the disaccharide sophorose, induce cellulase synthesis by *Trichoderma reesei*. Conversely, the presence of glucose results in tight repression of cellulase gene expression. Providing the appropriate inducer for industrial scale production is a major problematic factor contributing to high production costs of cellulase enzymes.

It has now been discovered that when a whole cellulase preparation is added to a concentrated glucose solution, and the composition is incubated for at least two days at about 50° C. to about 75° C., preferably about 50° C. to 65° C., a sugar mixture containing appreciable quantities of an inducer of cellulase gene expression is made, i.e, the inducing feed composition. The inducing feed composition has between about 2 and 25 g/L sophorose. In addition, the inducing feed composition has between about 35 and 60 g/L gentiobiose. Surprisingly, the resulting mixture does not need any further purification. It is competent to induce cellulase production as is. This discovery provides the inexpensive alternative to lactose or purified sophorose that is needed by industry, as well as a less cumbersome alternative to solid cellulose for the production of proteins regulated by inducible promoters in a filamentous fungus. It is specifically contemplated that the inventive composition is useful for cellulase production in *Trichoderma*.

In an alternative method of producing the inducing feed composition, the end fermentation broth (whole cellulase plus cells) may be added to a glucose solution (e.g., 20%). The presence of the cells does not affect sophorose formation. Thus, there is no need to use a recovered cellulase (i.e., a cellulase preparation isolated from the cells). The enzyme mixture present at the end of a fermentation may be used although the cells are still present.

In one embodiment, the invention provides a composition comprising a concentrated glucose solution and whole cellulase preparation that can be used as an inducing feed for the production of a protein of interest by a filamentous fungus. In one aspect, the protein of interest is a cellulolytic enzyme. In another aspect, the protein of interest is a heterologous protein. In an embodiment the inducing feed induces cellulase enzyme production by *Trichoderma reesei*. It is surprising that the solution is effective at inducing cellulase gene expression, since cellulase genes are known to be repressed by the presence of glucose.

In one embodiment an inducing feed is made by preparing a sterile solution of 5%-75% (wt/wt) glucose. A whole cellulase preparation from *Trichoderma reesei* is added to a sterile glucose solution to a final concentration of between 2 g and 20 g total protein/L. The final protein range may be as low as 0.5 g/L and as high as 50 g/L. In one aspect the β-glucosidase activity in the glucose solution is greater than 1.5 IU/ml. In one aspect the β-glucosidase activity in the glucose solution is less than 200 IU/ml. In another aspect β-glucosidase activity of the glucose solution is between 1.5 IU/ml and 200 IU/ml. In another aspect β-glucosidase activity of the glucose solution is between 1.9 IU/ml and 200 IU/ml. In another aspect β-glucosidase activity of the glucose solution is between 9.3 IU/ml and 200 IU/ml. In another aspect β-glucosidase activity of the glucose solution is between 1.5 IU/ml and 180 IU/ml. In another aspect β-glucosidase activity of the glucose solution is between 9.3 IU/ml and 180 IU/ml. The solution is incubated at 50° C.-75° C., preferably between 50° C. and 65° C. The solution is incubated for between 8 hours and 7 days with mixing. In one embodiment the incubation period is greater than two days. In second embodiment the incubation period is two days. In third embodiment the incubation period is three days. The final sterile solution is harvested and used for fermentation feeding. In one embodiment the inducing feed is prepared with a 60% (wt/wt) glucose solution. In another embodiment the inducing feed is prepared by adding whole cellulase preparation to the glucose solution to a final concentration of 2 g total protein/L.

Another object of the invention herein is to provide for the expression and secretion by the host filamentous fungus of desired proteins heterologous to said host filamentous fungus. The proteins produced by the induction of genes whose expression is controlled by an inducible promoter sequence include naturally occurring cellulase proteins, as well as various heterologous proteins. In a preferred embodiment, the protein expressed under control of inducible promoter sequences is a hormone, enzyme, growth factor, cytokine, or antibody.

Various species of filamentous fungi may be used as expression hosts including the following genera: *Aspergillus, Trichoderma, Neurospora, Penicillium, Cephalosporium, Achlya, Podospora, Endothia, Mucor, Cochliobolus* and *Pyricularia*. Specific expression hosts include *Trichoderma reesei*, e.g. NRRL 15709, ATCC 13631, 56764, 56765, 56466, 56767, *Trichoderma viride*, e.g., ATCC 32098 and 32086 *Aspergillus nidulans*, (Yelton, M., et al. (1984) Proc. Natl. Acad. Sci. USA, 81, 1470-1474; Mullaney, E. J. et al. (1985) Mol. Gen. Genet. 199, 37-45; John, M. A. and J. F. Peberdy (1984) Enzyme Microb. Technol. 6, 386-389; Tilburn, et al. (1982) Gene 26, 205-221; Ballance, D. J. et al., (1983) Biochem. Biophys. Res. Comm. 112, 284-289; Johnston, I. L. et al. (1985) EMBO J. 4, 1307-1311) *A. niger*, (Kelly, J. M. and M. Hynes (1985) EMBO 4, 475-479) *Aspergillus awamori*, e.g., NRRL 3112, ATCC 22342, ATCC 44733, ATCC 14331 and strain UVK 143f, *Aspergillus oryzae*, e.g., ATCC 11490, and *Neurospora crassa* (Case, M. E. et al. (1979) Proc. Natl. Acad. Scie. USA, 76, 5259-5263; Lambowitz U.S. Pat. No. 4,486,553; Kinsey, J. A. and J. A. Rambosek (1984) Molecular and Cellular Biology 4, 117-122; Bull, J. H. and J. C. Wooton (1984) Nature 310, 701-704).

In a preferred embodiment, the microbial host is a member of the species of *Trichoderma, Humicola, Fusarium, Aspergillus, Streptomyces, Thermomonospora, Bacillus,* or *Cellulomonas*.

I. DEFINITIONS

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody or its functional equivalent will be most critical in specificity and affinity of binding. See Paul, Fundamental Immunology.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

"Cellulase," "cellulolytic enzymes" or "cellulase enzymes" means bacterial, or fungal exoglucanases or exo-cellobiohydrolases, and/or endoglucanases, and/or β-glucosidases. These three different types of cellulase enzymes act synergistically to convert cellulose and its derivatives to glucose.

Many microbes make enzymes that hydrolyze cellulose, including the wood rotting fungus *Trichoderma*, the compost bacteria *Thermomonospora* (now *Thermobifida*), *Bacillus*, and *Cellulomonas; Streptomyces*; and the fungi *Humicola, Aspergillus* and *Fusarium*. The enzymes made by these microbes are mixtures of proteins with three types of actions useful in the conversion of cellulose to glucose: endoglucanases (EG), cellobiohydrolases (CBH), and beta-glucosidase (BG).

As used herein, the phrases "whole cellulase preparation" and "whole cellulase composition" are used interchangeably and refer to both naturally occurring and non-naturally occurring compositions. A "naturally occurring" composition is one produced by a naturally occurring source and which comprises one or more cellobiohydrolase-type, one or more endoglucanase-type, and one or more β-glucosidase components wherein each of these components is found at the ratio produced by the source. A naturally occurring composition is one that is produced by an organism unmodified with respect to the cellulolytic enzymes such that the ratio of the component enzymes is unaltered from that produced by the native organism.

A "non-naturally occurring" composition encompasses those compositions produced by: (1) combining component cellulolytic enzymes either in a naturally occurring ratio or non-naturally occurring, i.e., altered, ratio; or (2) modifying an organism to overexpress or underexpress one or more cellulolytic enzyme; or (3) modifying an organism such that at least one cellulolytic enzyme is deleted.

The whole cellulase mixtures useful in the present invention may have one or more of the various EGs and/or CBHs deleted. For example, EG1 may be deleted alone or in combination with other EGs and/or CBHs. BGs may be overexpressed relative to the native levels. Heterologous expression of BGs is also contemplated herein.

"Carbon limitation" is a state wherein a microorganism has just enough carbon to produce a desired protein product, but not enough carbon to completely satisfy the organism's requirement, e.g., sustain growth. Therefore, the maximal amount of carbon goes toward protein production.

As used herein, the terms "promoter" and "cellulase promoter" refers to a nucleic acid sequence that functions to direct transcription of a downstream gene and are used interchangeably herein. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. In one aspect the promoter is an inducible promoter. In another aspect the promoter is inducible by an inducer selected from the group consisting of gentiobiose, cellulose and sophorose. In one aspect the promoter is the *T. reesei* cbh1 promoter which is deposited in GenBank under Accession Number D86235. In another aspect the promoter is a cbh II or xylanase promoter from *T. reesei*.

As used herein, a "promotor sequence" is a DNA sequence which is recognized by the particular filamentous fungus for expression purposes. A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A "constitutive" promoter is a promoter that is active under most environmental and developmental conditions. An "inducible" promoter is a promoter that is active under environmental or developmental regulation. An example of an inducible promoter useful in the present invention is the *T. reesei* cbh 1 promoter. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

Examples include the promoter from the *A. awamori* or *A. niger* glucoamylase genes (Nunberg, J. H. et al. (1984) Mol. Cell. Biol. 4, 2306-2315; Boel, E. et al. (1984) EMBO J. 3, 1581-1585), the *Mucor miehei* carboxyl protease gene herein, the *Trichoderma reesei* cellobiohydrolase I gene (Shoemaker, S. P. et al. (1984) European Patent Application No. EP00137280A1), the *A. nidulans* trpC gene (Yelton, M. et al. (1984) Proc. Natl. Acad. Sci. USA 81, 1470-1474; Mullaney, E. J. et al. (1985) Mol. Gen. Genet. 199, 37-45) the *A. nidulans* alcA gene (Lockington, R. A. et al. (1986) Gene 33, 137-149), the *A. nidulans* tpiA gene (McKnight, G. L. et al. (1986) Cell 46, 143-147), the *A. nidulans* amdS gene (Hynes, M. J. et al. (1983) Mol. Cell Biol. 3, 1430-1439), the *T. reesei* xln1 gene, the *T. reesei* cbh2 gene, the *T. reesei* eg1 gene, the *T. reesei* eg2 gene, the *T. reesei* eg3 gene, and higher eukaryotic promoters such as the SV40 early promoter (Barclay, S. L. and E. Meller (1983) Molecular and Cellular Biology 3, 2117-2130).

A nucleic acid is "operably linked" when it is placed into a functional relationship with another nucleic acid sequence. For example, DNA encoding a secretory leader, i.e., a signal peptide, is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

The gene may encode therapeutically significant proteins or peptides, such as growth factors, cytokines, ligands, receptors and inhibitors, as well as vaccines and antibodies. The gene may encode commercially important industrial proteins or peptides, such as enzymes, e.g., proteases, mannanases, xylanases, amylases, glucoamylases, cellulases, oxidases and lipases. The gene of interest may be a naturally occurring gene, a mutated gene or a synthetic gene.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

"Induction" refers to the increased transcription of a gene resulting in the synthesis of a protein of interest in a cell or organism at a markedly increased rate in response to the presence of an "inducer". To measure the induction of a protein of interest, cells treated with a potential inducer are compared to control samples without the inducer. Control samples (untreated with inducers) are assigned a relative protein activity value of 100%. Induction of a polypeptide is achieved when the activity value relative to the control (untreated with inducers) is greater than 100%, greater than 110%, more preferably 150%, more preferably 200-500% (i.e., two to five fold higher relative to the control), or more preferably 1000-3000% higher.

The "filamentous fungi" of the present invention are eukaryotic microorganisms and include all filamentous forms of the subdivision Eumycotina (see Alexopoulos, C. J. (1962), Introductory Mycology, New York: Wiley). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligately aerobic. In contrast, vegetative growth by yeasts such as *S. cerevisiae* is by budding of a unicellular thallus, and carbon catabolism may be fermentative. *S. cerevisiae* has a prominent, very stable diploid phase, whereas diploids exist only briefly prior to meiosis in filamentous fungi, e.g., *Aspergillus* and *Neurospora*. *S. cervisiae* has 17 chromosomes as opposed to 8 and 7 for *A. nidulans* and *N. crassa* respectively. Recent illustrations of differences between *S. cerevisiae* and filamentous fungi include the inability of *S. cerevisiae* to process *Aspergillus* and *Trichoderma* introns and the inability to recognize many transcriptional regulators of filamentous fungi (Innis, M. A. et al. (1985) Science, 228, 21-26).

"Glucosidases" refers to any enzyme whose end product is glucose.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

An "incubation product" refers to a solution that was held or incubated at an elevated temperature for a specific period of time.

An "inducer" is any compound that causes cells to produce larger amounts of enzymes or other substances than they would otherwise produce if the inducer was absent.

"Inducing feed", refers to a solution fed to a microorganism that causes or induces the production of the desired protein product.

The terms "isolated" or "purified" as used herein refer to a nucleic acid or amino acid that is removed from at least one component with which it is naturally associated.

II. PROTEIN OF INTEREST OR DESIRED PROTEIN

The terms protein of interest and desired protein may be used interchangeably herein. The present invention is particularly useful in enhancing the intracellular and/or extracellular production of proteins. The protein may be homologous or heterologous. Proteins that may produced by the instant invention include, but are not limited to, hormones, enzymes, growth factors, cytokines, antibodies and the like.

Hormones include, but are not limited to, follicle-stimulating hormone, luteinizing hormone, corticotropin-releasing factor, somatostatin, gonadotropin hormone, vasopressin, oxytocin, erythropoietin, insulin and the like.

Growth factors are proteins that bind to receptors on the cell surface, with the primary result of activating cellular proliferation and/or differentiation. Growth factors include, but are not limited to, platelet-derived growth factor, epidermal growth factor, nerve growth factor, fibroblast growth factors, insulin-like growth factors, transforming growth factors and the like.

Cytokines are a unique family of growth factors. Secreted primarily from leukocytes, cytokines stimulate both the humoral and cellular immune responses, as well as the activation of phagocytic cells. Cytokines include, but are not limited to, colony stimulating factors, the interleukins (IL-1 ($\alpha$ and $\beta$), IL-2 through IL-13) and the interferons ($\alpha$, $\beta$ and $\gamma$).

Human Interleukin-3 (IL-3) is a 15 kDa protein containing 133 amino acid residues. IL-3 is a species specific colony stimulating factor which stimulates colony formation of megakaryocytes, neutrophils, and macrophages from bone marrow cultures.

Antibodies include, but are not limited to, immunoglobulins from any species from which it is desirable to produce large quantities. It is especially preferred that the antibodies are human antibodies. Immunoglobulins may be from any class, i.e., G, A, M, E or D.

Additionally, a "protein of interest" or "polypeptide of interest" refers to the protein to be expressed and secreted by the host cell. The protein of interest may be any protein that up until now has been considered for expression in prokaryotes. In one embodiment, the protein of interest which is expressed and secreted include proteins comprising a signal peptide. The protein of interest may be either homologous or heterologous to the host. Thus, a protein of interest may be a secreted polypeptide particularly an enzyme which is selected from amylolytic enzymes, proteolytic enzymes, cellulolytic enzymes, oxido-reductase enzymes and plant wall degrading enzymes. Examples of these enzymes include amylases, proteases, xylanases, lipases, laccases, phenol oxidases, oxidases, cutinases, cellulases, hemicellulases, esterases, perioxidases, catalases, glucose oxidases, phytases, pectinases, glucosidases, isomerases, transferases, galactosidases and chitinases. The secreted polypeptide may also be a hormone, a growth factor, a receptor, vaccine, antibody or the like. In an embodiment the secreted polypeptide is a cellulolytic enzyme.

III. MOLECULAR BIOLOGY

In one embodiment this invention provides for the expression of heterologous genes under control of the cellulase gene promoters of *Trichoderma reesei*. Therefore, this invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and Ausubel et al., eds., *Current Protocols in Molecular Biology* (1994)).

Heterologous genes comprising the cellulase gene promoter sequences of filamentous fungi are typically cloned into intermediate vectors before transformation into *Trichoderma reesei* cells for replication and/or expression. These intermediate vectors are typically prokaryotic vectors, e.g., plasmids, or shuttle vectors.

To obtain high level expression of a cloned gene, the heterologous gene is preferably positioned about the same distance from the promoter as is in the naturally occurring cellulase gene. As is known in the art, however, some variation in this distance can be accommodated without loss of promoter function.

Those skilled in the art are aware that a natural promoter can be modified by replacement, substitution, addition or elimination of one or more nucleotides without changing its function. The practice of the invention encompasses and is not constrained by such alterations to the promoter.

The expression vector/construct typically contains a transcription unit or expression cassette that contains all the additional elements required for the expression of the heterologous sequence. A typical expression cassette thus contains a promoter operably linked to the heterologous nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

The practice of the invention is not constrained by the choice of promoter in the genetic construct. However, exemplary promoters are the *Trichoderma reesei* cbh1, cbh2, eg1, eg2, eg3, eg5, xln1 and xln2 promoters.

In addition to a promoter sequence, the expression cassette should also contain a transcription termination region downstream of the structural gene to provide for efficient termination. The termination region may be obtained from the same gene as the promoter sequence or may be obtained from different genes.

Although any fungal terminator is likely to be functional in the present invention, preferred terminators include: the terminator from *Aspergillus nidulans* trpC gene (Yelton, M. et al. (1984) PNAS USA 81:1470-1474, Mullaney, E. J. et al. (1985) MGG 199:37-45), the *Aspergillus awamori* or *Aspergillus niger* glucoamylase genes (Nunberg, J. H. et al. (1984) Mol. Cell Biol. 4:2306, Boel, E. et al. (1984) EMBO J. 3:1581-1585) and the *Mucor miehei* carboxyl protease gene (EPO Publication No. 0 215 594).

The particular expression vector used to transport the genetic information into the cell is not particularly critical. Any of the conventional vectors used for expression in eukaryotic or prokaryotic cells may be used. Standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

The elements that are typically included in expression vectors also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable. The prokaryotic sequences are preferably chosen such that they do not interfere with the replication or integration of the DNA in *Trichoderma reesei*.

The methods of transformation of the present invention may result in the stable integration of all or part of the transformation vector into the genome of the filamentous fungus. However, transformation resulting in the maintenance of a self-replicating extra-chromosomal transformation vector is also contemplated.

Many standard transfection methods can be used to produce *Trichoderma reesei* cell lines that express large quantities of the heterologus protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138).

However, any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the heterologous gene.

After the expression vector is introduced into the cells, the transfected cells are cultured under conditions favoring expression of genes under control of cellulase gene promoter sequences. Large batches of transformed cells can be cultured as described below. Finally, product is recovered from the culture using standard techniques.

Thus, the invention herein provides for the expression and enhanced secretion of desired polypeptides whose expression is under control of cellulase gene promoter sequences including naturally occurring cellulase genes, fusion DNA sequences, and various heterologous constructs. The invention also provides processes for expressing and secreting high levels of such desired polypeptides.

IV. FILAMENTOUS FUNGI

Filamentous fungi include all filamentous forms of the subdivision Eumycota and Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

In the present invention, the filamentous fungal parent cell may be a cell of a species of, but not limited to, *Trichoderma*, e.g., *Trichoderma longibrachiatum (reesei), Trichoderma viride, Trichoderma koningii, Trichoderma harzianum; Penicillium* sp.; *Humicola* sp., including *Humicola insolens; Chrysosporium* sp., including *C. lucknowense; Gliocladium* sp.; *Aspergillus* sp.; *Fusarium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*.

In one preferred embodiment, the filamentous fungal parent cell is an *Aspergillus niger, Aspergillus awamori, Aspergillus aculeatus,* or *Aspergillus nidulans* cell.

In another preferred embodiment, the filamentous fungal parent cell is a *Trichoderma reesei* cell.

V. PROTEIN EXPRESSION

Proteins of the present invention are produced by culturing cells transformed with an expression vector containing genes whose expression is under control of cellulase gene promoter sequences. The present invention is particularly useful for enhancing the intracellular and/or extracellular production of proteins. The protein may be homologous or heterologous. Proteins that may produced by the instant invention include, but are not limited to, hormones, enzymes, growth factors, cytokines, antibodies and the like.

Enzymes include, but are not limited to, hydrolases, such as protease, esterase, lipase, phenol oxidase, permease, amylase, pullulanase, xylanase, cellulase, glucose isomerase, laccase and protein disulfide isomerase.

Hormones include, but are not limited to, follicle-stimulating hormone, luteinizing hormone, corticotropin-releasing factor, somatostatin, gonadotropin hormone, vasopressin, oxytocin, erythropoietin, insulin and the like.

Growth factors are proteins that bind to receptors on the cell surface, with the primary result of activating cellular proliferation and/or differentiation. Growth factors include, but are not limited to, platelet-derived growth factor, epidermal growth factor, nerve growth factor, fibroblast growth factors, insulin-like growth factors, transforming growth factors and the like.

Cytokines are a unique family of growth factors. Secreted primarily from leukocytes, cytokines stimulate both the humoral and cellular immune responses, as well as the activation of phagocytic cells. Cytokines include, but are not limited to, colony stimulating factors, the interleukins (IL-1 $\alpha$ and $\beta$, IL-2 through IL-13) and the interferons ($\alpha$, $\beta$ and $\gamma$).

Human Interleukin-3 (IL-3) is a 15 kDa protein containing 133 amino acid residues. IL-3 is a species specific colony stimulating factor which stimulates colony formation of megakaryocytes, neutrophils, and macrophages from bone marrow cultures.

Antibodies include, but are not limited to, immunoglobulins from any species from which it is desirable to produce large quantities. It is especially preferred that the antibodies are human antibodies. Immunoglobulins may be from any class, i.e., IgG, IgM, IgA, IgD or IgE.

Proteins of interest in the present invention may also be modified in a way to form chimeric molecules comprising a protein of interest fused to another, heterologous polypeptide or amino acid sequence. In one embodiment, such a chimeric molecule comprises a fusion of the protein of interest with a tag polypeptide which provides an epitope to which an anti-tag antibody can selectively bind. The epitope tag is generally placed at the amino- or carboxyl-terminus of the protein of interest.

Various tag polypeptides and their respective antibodies are well known in the art. Examples include poly-histidine (poly-his) or poly-histidine-glycine (poly-his-gly) tags; HIS6 and metal chelation tags, the flu HA tag polypeptide and its antibody 12CA5 (Field et al., *Mol. Cell. Biol.* 8:2159-2165 (1988)); the c-myc tag and the 8F9, 3C7, 6E10, G4, B7 and 9E10 antibodies thereto (Evan et al., *Molecular and Cellular Biology* 5:3610-3616 (1985)); and the Herpes Simplex virus glycoprotein D (gD) tag and its antibody (Paborsky et al., Protein Engineering 3(6):547-553 (1990)). Other tag polypeptides include the FLAG-peptide (Hopp et al., *Bio-Technology* 6:1204-1210 (1988)); the KT3 epitope peptide (Martin et al., *Science* 255:192-194 (1992)); tubulin epitope peptide (Skinner et al., *J. Biol. Chem.* 266:15163-15166 (1991)); and the T7 gene 10 protein peptide tag (Lutz-Freyermuth et al., *Proc. Natl. Acad. Sci. USA* 87:6393-6397 (1990)).

In an alternative embodiment, the chimeric molecule may comprise a fusion of a protein of interest with an immunoglobulin or a particular region of an immunoglobulin. For a bivalent form of the chimeric molecule, such a fusion could be to the Fc region of an IgG molecule.

Conditions appropriate for expression of said genes comprise providing to the culture an inducing feed composition of the instant invention. Optimal conditions for the production of the proteins will vary with the choice of the host cell, and with the choice of protein to be expressed. Such conditions will be easily ascertained by one skilled in the art through routine experimentation or optimization.

The protein of interest is typically purified or isolated after expression. The protein of interest may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the protein of interest may be purified using a standard anti-protein of interest antibody column. Ultrafiltration and diafiltration techniques, in conjunction with protein concentration, are also useful. For general guidance in suitable purification techniques, see Scopes, Protein Purification (1982). The degree of purification necessary will vary depending on the use of the protein of interest. In some instances no purification will be necessary.

VI. FERMENTATION

The invention relies on fermentation procedures for culturing fungi and bacteria. Fermentation procedures for production of cellulase enzymes are known per se in the art. For example, cellulase enzymes can be produced either by solid or submerged culture, including batch, fed-batch and continuous-flow processes.

Culturing is accomplished in a growth medium comprising an aqueous mineral salts medium, organic growth factors, the carbon and energy source material, molecular oxygen, and, of course, a starting inoculum of one or more particular microorganism species to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation media.

The composition of the aqueous mineral medium can vary over a wide range, depending in part on the microorganism and substrate employed, as is known in the art. The mineral media should include, in addition to nitrogen, suitable amounts of phosphorus, magnesium, calcium, potassium, sulfur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

The fermentation reaction is an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion. In effect, by using an oxygenated hydrocarbon substrate, the oxygen requirement for growth of the microorganism is reduced. Nevertheless, molecular oxygen must be supplied for growth, since the assimilation of the substrate and corresponding growth of the microorganisms, is, in part, a combustion process.

Although the aeration rate can vary over a considerable range, aeration generally is conducted at a rate which is in the range of about 0.5 to 10, preferably about 0.5 to 7, volumes (at the pressure employed and at 25° C.) of oxygen-containing gas per liquid volume in the fermentor per minute. This amount is based on air of normal oxygen content being supplied to the reactor, and in terms of pure oxygen the respective ranges would be about 0.1 to 1.7, or preferably about 0.1 to 1.3, volumes (at the pressure employed and at 25° C.) of oxygen per liquid volume in the fermentor per minute.

The pressure employed for the microbial conversion process can range widely. Pressures generally are within the range of about 0 to 50 psig, presently preferably about 0 to 30 psig, more preferably at least slightly over atmospheric pressure, as a balance of equipment and operating cost versus oxygen solubility achieved. Greater than atmospheric pressures are advantageous in that such pressures do tend to increase a dissolved oxygen concentration in the aqueous ferment, which in turn can help increase cellular growth rates. At the same time this is balanced by the fact that high atmospheric pressures do increase equipment and operating costs.

The fermentation temperature can vary somewhat, but for filamentous fungi such as *Trichoderma reesei* the temperature generally will be within the range of about 20° C. to 40° C., generally preferably in the range of about 25° C. to 34° C., depending on the strain of microorganism chosen.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. With filamentous fungi, the pH normally is within the range of about 2.5 to 8.0; with *Trichoderma reesei*, the pH normally is within the range of about 3.0 to 7.0. pH range preferences for certain microorganisms are dependent on the media employed to some extent, as well as the particular microorganism, and thus change somewhat with change in media as can be readily determined by those skilled in the art.

While the average retention time of the fermentation admixture in the fermentor can vary considerably, depending in part on the fermentation temperature and culture employed, generally it will be within the range of about 24 to 500 hours, preferably presently about 24 to 400 hours.

Preferably, the fermentation is conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily washed off. It may be a problem, however, in the case of non-water-soluble substrates, and require added product-treatment steps such as suitable washing steps.

As described above, the time to reach this level is not critical and may vary with the particular microorganism and fermentation process being conducted. However, it is well known in the art how to determine the carbon source concentration in the fermentation medium and whether or not the desired level of carbon source has been achieved.

Although the fermentation can be conducted as a batch or continuous operation, fed batch operation is much to be preferred for ease of control, production of uniform quantities of products, and most economical uses of all equipment.

If desired, part or all of the carbon and energy source material and/or part of the assimilable nitrogen source such as ammonia can be added to the aqueous mineral medium prior to feeding the aqueous mineral medium to the fermentor.

Each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermentor, cell density measurable by light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermentor employed is not critical, though presently preferred is operation under 15 L Biolafitte (Saint-Germain-en-Laye, France).

The collection and purification of the cellulose enzymes from the fermentation broth can also be done by procedures known per se in the art. The fermentation broth will generally contain cellular debris, including cells, various suspended solids and other biomass contaminants, as well as the desired cellulase enzyme product, which are preferably removed from the fermentation broth by means known in the art.

Suitable processes for such removal include conventional solid-liquid separation techniques such as, e.g., centrifugation, filtration, dialysis, microfiltration, rotary vacuum filtration, or other known processes, to produce a cell-free filtrate. It may be preferable to further concentrate the fermentation broth or the cell-free filtrate prior to crystallization using techniques such as ultrafiltration, evaporation or precipitation.

Precipitating the proteinaceous components of the supernatant or filtrate may be accomplished by means of a salt, e.g., ammonium sulfate, followed by purification by a variety of chromatographic procedures, e.g., ion exchange chromatography, affinity chromatography or similar art recognized procedures.

EXAMPLES

The following examples are offered to illustrate, but not to limit the claimed invention.

Example 1

This example illustrates how an inducing feed composition for stimulating the expression of cellulase genes in *Trichoderma reesei* was prepared. The incubation was run at the pH of the solution, i.e., 5.0. For beta-glucosidase the incubation was found to be best at pH 4.0-6.5.

(i) A 60% (w/w) glucose solution was sterilized for 30 minutes at 121° C., 2.2 bar pressure.

(ii) Sterile whole cellulase preparation was added to the glucose solution to a final concentration of 10 g total protein/L.

(iii) The tank containing the glucose and whole cellulase mixture was held at 65° C. for 3 days with 75 RPM mixing.

(iv) Following incubation, the sterile solution was harvested to an appropriate container for fermentation feeding.

The resulting inducing feed composition was found to have 16.1 g/L Sophorose, 47.5 g/L Gentiobiose, and approximately 600 g/L Glucose. Other sugars may be present but were not analyzed.

Inducing feed solutions have also been prepared from solutions of 20% and 60% glucose. The higher the glucose solution, the higher the final sophorose concentration.

Whole cellulase preparation has been used at final concentrations of 2 g and 10 g total protein/L. The higher the protein loading, the higher the ending sophorose concentration. See FIG. 6. Ultimately however, it is expected that a longer reaction at the lower concentration of whole cellulase preparation will achieve the same sophorose levels if the solution is incubated for a longer period of time.

The incubation temperature also influences sophorose production. For example, sophorose concentration was 2 times as high when the composition was incubated at 65° C. than when the composition was incubated at 50° C.

Example 2

The following example details how a glucose/sophorose feed is made and used to produce cellulase enzyme during fermentation.

I. Production of Glucose/Sophorose Feed:

60% (w/w) glucose solution was dissolved and sterilized for 30 minutes at 121° C. The temperature was decreased to 65° C. and 10 g of total protein (whole cellulase previously produced by *T. reesei*)/L was added. The mixture was agitated slowly and held at 65° C. for 3 days. The sophorose content was measured at 12 g/L in this 60% glucose solution.

II. Fermentation 0.8 L of media was inoculated with 1.5 ml *Trichoderma reesei* RL-P37 frozen spore suspension as a seed flask. This flask was split into two 0.4 L portions and transferred to 2×7 L of fermentation media in two different 15 L Biolafitte fermentors after 48 hours. The growth media had the following composition:

| Media component | g/L |
|---|---|
| $KH_2PO_4$ | 4 |
| $(NH_4)2SO_4$ | 6.35 |
| $MgSO_4$—$7H_2O$ | 2 |
| $CaCl_2$—$2H_2O$ | 0.53 |
| Glucose | 50 |
| Corn Steep Solids (Roquette) | 6.25 |
| Trace elements* | 1 ml/L |

Trace elements*: 5 g/L $FeSO_4$—$7H_2O$; 1.6 g/L $MnSO_4$—$H_2O$; 1.4 g/L $ZnSO_4$—$7H_2O$.

The fermentor was run at 25° C., 750 RPM and 8 standard liters per minute (SLM) airflow.

The glucose/sophorose was added in place of glucose in the batch phase for the experimental tank but pure glucose was used in the control. This batched glucose was exhausted at approximately 20 hours at which point the cells stopped growing and a carbon limiting feed was begun. A 40% glucose/sophorose feed was added at 0.25 g/minute with 40% pure glucose solution being fed to the control tank (diluted from feed formation detailed above). Total protein, which is directly correlated with cellulase production (based upon our comparison of total extracellular protein vs cellulase activity), was induced just after the batch phase in the glucose/sophorose tank but not in the glucose control tank. Thus, pretreatment of the glucose with whole cellulase is required to produce cellulase on glucose with *Trichoderma reesei* RL-P37. See FIG. 1.

Example 3

The following example details how a glucose/sophorose feed is made and used to produce a heterologous protein from a filamentous fungus during fermentation.

The inducing feed composition is prepared using the procedure in Example 1.

An expression plasmid for use in transforming *Trichoderma reesei* is constructed as follows. The ends of the gene encoding protein of interest are blunted by T4 DNA polymerase and inserted into PmeI restriction site of the *Trichoderma* expression vector, pTEX, see PCT Publication No. WO 96/23928, which publication is herein incorporated by reference, which contains a CBHI promoter and terminator for gene expression and a *Trichoderma* pyr4 gene as a selection marker for transformants. The linear DNA fragment containing only the CBH1 promoter, the gene encoding the protein of interest, the CBH1 terminator and selection marker pyr4 is isolated from a gel and used to transform a uridine auxotroph strain of *Trichoderma reesei* (see U.S. Pat. No. 5,472,864) which has the four major cellulase genes deleted. Stable transformants are isolated on *Trichoderma* minimal plates without uridine. The transformants are grown on 50 ml of Proflo medium in shake flasks for 4 days at 28° C. to 30° C. and expression of the protein of interest is assayed by methods known to one skilled in the art. Proflo medium is composed of (g/l) Proflo 22.5; lactose 30.0; $(NH_4)_2SO_4$ 6.5

$KH_2PO_4$ 2.0; $MgSO_4.7H_2O$ 0.3; $CaCL_2$ 0.2; $CaCO_3$ 0.72; trace metal stock solution 1.0 ml/l and 10% Tween 80 2.0 ml/l. The trace metal stock solution used had (g/l) $FeSO_4.7H_2O$ 5.0; $MnSO_4.H_2O$ 1.6; $ZnSO_4.7H_2O$ 1.4; $CoCl_2.6H_2O$) 2.8.

The shake flasks are divided and placed in a 15 L fermentor as described in Example 2. Expression of the protein of interest is induced by the inducing feed composition but not the glucose solution.

Example 4

This example details how the enzyme may be immobilized for the production of an inducing feed solution.

A whole cellulase broth comprising a β-glucosidase is immobilized according to the method described in U.S. Pat. No. 5,541,097. Briefly, 10 gm of bentonite were in 500 ml water to which 11 ml of 10% PEI was added. Separately 20 ml of whole cellulase (200 g Total Protein/L) was added to 250 ml of 0.02 M acetate buffer at pH 5.5. Then 4.44 ml of 50% Glutaraldehyde (Fischer, Reagent Grade) was added to the enzyme solution while the pH was maintained at 5.5. After 2 hours the enzyme complex was added to the bentonite complex giving a total volume of about 750 ml. This mixture was mixed overnight at 4° C. The complex was then collected on a Buchner funnel and washed with a large quantity of water. The cake was then resuspended in 0.02 M acetate buffer, with a final weight of 175 gm.

It is difficult to quantitate the enzyme activity remaining after immobilization because whole cellulase contains greater than five different enzymes, each with different activities (the immobilized enzyme was shown to reduce the viscosity of barley flour slurry, so cellulase activity was known to be present). Therefore, cellulase loading was done based upon how much enzyme was immobilized, not how much remained active. The final slurry was determined to contain 0.022 g total protein/g slurry.

Sophorose production from the immobilized cellulase was examined at two different enzyme loading and glucose concentrations:

1) 23 g slurry+29.5 ml 67% (w/w) glucose=10 g/L protein loading @ 40.7% glucose
2) 7.6 g slurry+44.8 ml 67% (w/w) glucose=3.2 g/L protein loading @ 60% glucose Each 52.5 ml volume was added to a 250 ml Erlenmeyer flask, agitated at 100 RPM and incubated at 65° C. over several days.

The rate of sophorose production for each of the two cases was lower than the control case where the same amount of enzyme solution was added as immobilized enzyme (FIGS. 2-3). This was not surprising, as it is assumed that some of the enzyme activity is lost as the enzyme is immobilized. However, the large gain for immobilization is that the enzyme can be used to make multiple batches of glucose/sophorose feed. FIG. 4 shows that centrifuging the immobilized enzyme out of the glucose solution and repeating the experiment as shown above, the same final sophorose titers are achieved in the first and second trials. This shows that the enzyme is still active over at lease two uses, and likely over many more. Therefore, even with some loss of enzyme activity from immobilization, the ability to reuse the enzyme multiple times makes cellulase immobilization the most attractive alternative for glucose/sophorose production.

Example 5

This example details how the production of an inducing feed solution may be accomplished with the use of cellobiose as a starting carbon source.

The experiments were run in the exact same way as the other examples of sophorose production in shake flasks (50 ml in 250 ml flask, 65° C., 100 RPM) except for what is noted below. FIG. 5 compares the sophorose production in 25% cellobiose with that produced in 25% glucose.

If sophorose is the "true" inducer in nature, it would most likely have to be formed from cellobiose as *T. reesei* is very unlikely to see even moderate levels of glucose in nature which would be required to form sophorose via transglycosylation. FIG. 5 shows 25% (w/w) cellobiose incubated with 10 g/L cellulase compared to 25% glucose. The sophorose produced from cellobiose peaked at more than 10 g/L, three times the concentration that was produced by glucose alone. However, that sophorose was then degraded down to a similar level as that produced from glucose alone (4.1 g/L vs 2.5 g/L). This behavior seems to show the sophorose approaching an equilibrium with the glucose, which was all that remained after all of the cellobiose was cleaved around 29 hours.

It is highly unlikely that the β-glucosidase enzyme sees a sufficient concentration of glucose to form much sophorose in nature. The cells are more likely to see high concentrations of cellobiose, a breakdown product of cellulose. FIG. 5 shows that three times as much sophorose is produced from cellobiose than from glucose. The sophorose level appears to fall at the same time the cellobiose is completely turned over to glucose and other transglycosylation products at approximately 29 hours (cellobiose data not shown). This would support a hypothesized mechanism where the cellobiose is cleaved to two glucose molecules that then rearrange and transglycosylate before leaving the active site. As the cellobiose experiment continued, the rate of sophorose cleavage was greater than the rate of sophorose formation from glucose transglycosylation and the sophorose level fell to almost that of glucose, 4.1 g/L compared to 2.5 g/L. This data strongly supports the possibility that small amounts of sophorose are formed through the cleavage of cellobiose by β-glucosidase.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of producing an inducing feed composition capable of inducing the expression of a gene under the control of a sophorose-inducible promoter or a gentiobiose-inducible promoter, said method comprising the steps of:
   a. Providing a whole cellulase preparation which is an end fermentation broth;
   b. Mixing a concentrated glucose solution comprising from about 5% to about 75% glucose with the whole cellulase preparation of a. to give a first mixture; and
   c. Incubating the first mixture at a temperature and for a sufficient time to produce the inducing feed composition.

2. The method of claim 1 wherein the whole cellulase preparation includes about 2 g/L to about 10 g/L protein.

3. The method of claim 2 wherein the whole cellulase preparation includes about 5 g/L protein.

4. The method of claim 1 wherein the temperature is from about 50° C. to about 75° C.

5. The method of claim 1 wherein the sufficient time to produce the inducing feed composition is between 8 hours and 500 hours.

6. The method of claim 5, wherein the sufficient time to produce the inducing feed composition is between 48 hours and 72 hours.

7. The method of claim 1 wherein the whole cellulase preparation is immobilized.

8. The method of claim 1, wherein the whole cellulase preparation comprises one or more beta-glucosidase, one or more endoglucanase, and one or more cellobiohydrolase.

9. The method of claim 1, wherein the whole cellulase preparation is a naturally occurring composition.

10. The method of claim 1, wherein the whole cellulase preparation is a non-naturally occurring composition.

11. The method of claim 1, wherein the whole cellulase preparation is not a recovered cellulase from the fermentation broth.

\* \* \* \* \*